United States Patent [19]

Huc et al.

[11] Patent Number: 4,711,783

[45] Date of Patent: Dec. 8, 1987

[54] FORMS OF MICROENCAPSULATION OF MEDICINAL SUBSTANCES BY HOMOGENEOUS LAYERS OF NATIVE COLLAGEN

[75] Inventors: Alain Huc, Ste Foy-les-Lyons; Rene Gimeno, Pelussin; Daniel Herbage, Lyons, all of France

[73] Assignee: Bioetica, S.A., Lyons, France

[21] Appl. No.: 596,422

[22] Filed: Apr. 3, 1984

[51] Int. Cl.[4] .................. A61K 9/38; A61K 9/64; A61K 9/22; A61K 9/52

[52] U.S. Cl. .................. 424/460; 424/477; 424/491; 424/499; 106/155; 106/161; 530/356; 514/773; 514/774; 514/801

[58] Field of Search ............. 424/36, 460, 477, 491, 424/499, 37; 106/155, 161; 530/356; 514/773, 774, 801

[56] References Cited

U.S. PATENT DOCUMENTS

| | | | |
|---|---|---|---|
| 3,435,110 | 3/1969 | Nichols | 424/20 |
| 3,649,347 | 3/1972 | Battista | 424/36 |
| 3,955,012 | 5/1976 | Okamura et al. | 424/36 |
| 4,010,038 | 3/1977 | Iwasaki et al. | 424/37 |
| 4,107,288 | 8/1978 | Oppenheim et al. | 424/36 |
| 4,140,537 | 2/1979 | Luck et al. | 106/161 |
| 4,164,559 | 8/1979 | Miyata et al. | 424/36 |
| 4,233,360 | 11/1980 | Luck et al. | 514/801 |
| 4,291,013 | 9/1981 | Wahlig et al. | 424/36 |
| 4,426,443 | 1/1984 | Shank | 106/155 |
| 4,478,658 | 10/1984 | Wittwer | 427/3 |
| 4,488,911 | 12/1984 | Luck et al. | 106/161 |
| 4,536,387 | 8/1985 | Sakamoto | 514/774 |
| 4,591,456 | 5/1986 | Huc et al. | 106/161 |

FOREIGN PATENT DOCUMENTS 59-46215  3/1984  Japan .

OTHER PUBLICATIONS

Biochim. Biophysica Acta., 194 (1969), pp. 325–328, Herbage et al.

J. F. Woessner, Jr., Treatise on Collagen, Biological Mechanisms of Collagen Resorption, vol. 2, pp. 253–330, (1968).

A. Veis, Int. Rev. of Connective Tissue Research, vol. 3, pp. 113–200 (1965).

*Primary Examiner*—Shep K. Rose
*Attorney, Agent, or Firm*—Karl F. Ross; Herbert Dubno

[57] ABSTRACT

A new sustained-release, microencapsulated pharmaceutical composition is disclosed, suitable for oral administration which contains an effective amount of an orally-administered pharmaceutical in granular form wherein the granules are coated by a layer of homogeneous, native collagen to encapsulate the granules. Also disclosed is a method for administering the sustained-release compositions and a process for covering the granulated pharmaceutical with the layer of homogeneous, native collagen.

5 Claims, No Drawings

FORMS OF MICROENCAPSULATION OF MEDICINAL SUBSTANCES BY HOMOGENEOUS LAYERS OF NATIVE COLLAGEN

FIELD OF THE INVENTION

The invention relates to new forms of microencapsulation of medicinal substances using homogeneous layers of native collagen.

BACKGROUND OF THE INVENTION

A number of medicinal substances absorbed by the oral route must exert their effect only at the intestinal level and not before. Thus it is necessary that these substances remain for a given time in the stomach without these different agents acting on a level in the stomach so as to be completely digested.

Furthermore it is often desirable that the medicinal effect of an active substance be prolonged for a significant period of time in order to achieve a sustained-release effect.

For one or the other of these reasons or for both of these reasons together, it is very often necessary to protect the medicinal substance by a biodegradable and non-toxic covering, as a way to provide microencapsulation. Until now, resort has usually been made to microencapsulation techniques employing gelatine as a protecting agent.

It is known that gelatine is constituted by collagen, partially denatured and degraded by thermal, enzymatic, or chemical treatment. The treatments make the proteins vary fragile and the mean molecular mass of gelatine is lowered by rupture of the reticulated bonds and/or the peptide bonds. At best, the mean molecular mass is about 120,000; this lowering of the molecular mass considerably augments the solubility of the gelatine, especially in an aqueous medium, under the action of heat and acids. The gelatine does maintain a certain amount of the helicoidal structure, but this structure is more fragile than that of natural collagen. See A. Vers. Int. Rev. of Connective Tissue Research, Vol 3 (1965), 113-120. In effect the gelatinous material disappears even at temperatures less than 37° C. The partial structure of the gelatine is rapidly destroyed in the organism and no longer protects against enzymatic action, especially against the enzymes in gastric juices.

In the course of a number of studies carried out on native collagen, the investors came up with the idea of exploiting certain properties of the product, in order to obtain new forms of microencapsulation for medicinal substances permitting a sustained release of the latter that is a good deal more sustained than the release obtained when gelatine is used for the microencapsulation.

The mean molecular mass of a native collagen is equal to or greater than 300,000 daltons. The collagen macromolecule which is wider than 15 angstrom units and longer than 2990 angstroms units is constituted by 3 peptide chains each having a molecular mass of 10,000 daltons. It is characterized by the presence of a glycine residue in every third amino acid residue the molecule as well as by a high content of hydroxy-proline. Between the chains there exists covalent chemical bonds which are bonded on at least one side to the end of the peptide chain, call telopeptides. This latter part is not present in a helical coil structure having a length of about 50 angstroms units. The three peptide chains are wound in a triple helix around a common axis. It can be determined that in this triple helix structure, the presence of the reticulated bonds and the size of the macromolecules are the essential factors for the partial insolubility of the collagen and for its resistance to enzymes. In effect the proteolytic enzymes (with the exception of collagenase) do not act on the collagen structures and will only digest the telopeptides, which are not in helicoidal form. This is evidence of the role of the helicoidal structure of the collagen as a protector from enzymatic action. See J. F. Woessner, J. B. Treatise on Collagen, 1968, vol. 2, pp 252-330. The temperature where the helicoidal structure disappears is 37° C.

OBJECT OF THE INVENTION

It is the object of the invention to provide a new way to microencapsulate medicinal substances for sustained release.

SUMMARY OF THE INVENTION

The new forms used to carry out microencapsulation of medicaments are prepared through the use of homogeneous layers of native collagen to encapsulate said medicament.

The new forms of microencapsulate can be prepared by any known procedure to form a collagen coating. One can advantageously prepares such coatings according to the process disclosed in Applicants' French Patent Application 82 05997, which is equivalent to Applicants' concurrently filed U.S. application Ser. No. 738,910, now U.S. Pat. No. 4,591,456.

The process involves preparing an alcoholic solution of native collagen and in depositing it by spraying or by immersion and draining of the granules of the medicament to be covered.

The covered granules of medicament are next air-dried to form a homogeneous layer of native collagen thereon, and then the granular medicament with the homogeneous coating of native collagen is subjected to a thermal treatment under vacuum at 100° C. for 24 hours, to assure reticulation of the collagen. The alcohol is chosen from among the lower aliphatic alcohols, and is preferably methanol. Methanol is preferred because of its suitable vapor pressure which permits its rapid evaporation at temperatures lower than that of the deactivation of collagen, thus ensuring a uniform coating of the granules of the medicament.

PREPARATION OF THE ALCOHOLIC SOLUTION OF COLLAGEN

The acid-soluble, purified, lyophilized collagen is prepared for example according to the technique described by Herbage et al referred to hereinabove "Biochim. Biophys. Acta (1969) 325-328".

At first the chemical composition is verified to make sure that it is indeed collagen. In particular it is determined that the material contains about 333 glycine residues and about 100 hydroxy-proline residues per 1000 amino acid residues.

The determination of the molecular mass should not show a value of less than 100,000 daltons in the aqueous solution of the protein after heating to 40° C. Finally, an X-ray diffraction analysis examination as well as programmed differential calorimetry must confirm the entire triple helix structure characteristic of collagen.

3 grams of the collagen are dissolved in 1 liter of a solution of 0.5M acetic acid and the solution is agitated for at least 2 hours, the centrifuging is carried out at 14,000 g for 1 hours. The supernatant is then poured into acetone in a ratio of 1 liter per 5 liters of solvent. The collagen precipitates and the precipitate is separated by centrifuging at 3000 t/m in a centrifuge of the type Robatel CF 200. The precipitate is then dissolved in a mixture of methanol and a 0.5M aqueous acetic acid solution (50/50). After 1 hours of agitation, the total mixture is poured into an acetone bath at the rate of 1 liter of solution per 5 liters of solvent.

The precipitate is recovered as described hereinabove, then put back into solution in a mixture of methanol and a 0.5M aqueous acetic acid solution (80/20). After 1 hour of agitation, the mixture is poured into an acetone bath in a ratio of 1 liter of solution per 5 liters of solvent. The precipitate is dissolved and put into a methanol solution at the rate of 2 g/l. After centrifuging at 30,000 g for 1 hours, the solution is put into the supply reservoir of a spray gun-pulverizer of the type Kremlin J.M. operating under a pressure of 100 g.

OBTAINING GRANULES OF MEDICAMENT COVERED BY COLLAGEN

The following medicaments are obtained in granular form and are covered with the homogeneous layers of the native collagen according to the present invention;

(a) dextroamphetamine sulfate, (b) phenobarbital, and (c) a combination of 8 parts of chlorpheniramine maleate and 50 parts of phenylpropanolamine, a well-known medicament used against nasal congestion and usually administered in the form of a sustained-release capsule.

COVERING PROCESS, ITSELF 200 cc of the granules treated as described hereinabove are placed in a dragee-coater of the ERWEKA type of 10 liters, made of stainless steel, turning at a velocity of 60 t/m. The collagen solution in the methanol is applied by spraying onto the granules moving in the dragee-coater. 3 spraying operations are carried out each for 15 seconds, separated each time by drying for 30 minutes in the dragee-coater.

The quantity of the collagen deposited onto the granules can be determined according to the following: A known amount of the granules is placed in a 6N hydrochloric acid solution at 105° C. for 24 hours. Next the amount of hydroxy-proline obtained is determined according to the Stegmann method. The quantity of the deposited collagen is equal to the quantity of hydroxy-proline multiplied by 7.46.

It goes without saying that the present invention is not at all limited to the examples described hereinabove, which are nonlimiting; on the contrary, the invention includes all variations which might be particularly related to the nature or form of the medicament to be coated by the layers of homogeneous, layered collagen.

We claim:

1. A sustained-release, coated pharmaceutical composition, suitable for oral administration, which consists essentially of:
   (a) a pharmaceutically effective amount of an orally-administered medicament in granular form; and
   (b) a layer of homogeneous, native collagen coating said granules of medicament, said layer of homogeneous, native collagen applied to the granules of medicament by the following steps:
      (i) forming an acid-soluble methanolic solution of native collagen having a mean molecular mass equal to or greater than 300,000 Daltons, the collagen macromolecule having a width greater than 15 angstrom units and a length greater than 2990 angstrom units, constituted by 3 peptide chains wound around each other in a common helical axis, each having a molecular mass of 10,000 Daltons wherein every third amino acid residue is a glycine residue and having a high number of hydroxy-proline residues, between each of said peptide chains there exist covalent chemical bonds which are bonded on at least one side to the end of a peptide chain called a telopeptide, said telopeptide not present in the common helical axis and having a length of about 50 angstrom units, thereby providing a collagen that is partially insoluble and resistant to enzymes;
      (ii) applying the methanolic solution of native collagen formed in step (a) to the orally-administered medicament in granular form to cover the granular medicament with a homogeneous layer of native collagen;
      (iii) air-drying the coating on said granular medicament to a homogeneous layer of native collagen; and
      (iv) subjecting the granular medicament coated during step (c) and after air-drying to a thermal treatment under vacuum at 100° C. for 24 hours, to assure reticulation of the collagen.

2. A method of administering an orally-administered medicament in sustained-release form which comprises the step of orally administering to a patient in need of said medicament, a pharmaceutically effective amount of the sustained-release, pharmaceutical composition defined in claim 1.

3. The pharmaceutical composition defined in claim 1 wherein the medicament in granular form is dextroamphetamine sulfate.

4. The pharmaceutical composition defined in claim 1 wherein the medicament in granular form is phenobarbital.

5. The pharmaceutical composition defined in claim 1 wherein the medicament in granular form is a mixture of 8 parts of chlorpheniramine maleate and 50 parts of phenylpropanolamine.

* * * * *